(12) United States Patent
Sun et al.

(10) Patent No.: US 9,168,328 B2
(45) Date of Patent: Oct. 27, 2015

(54) LAYERED MANUFACTURING UTILIZING FOAM AS A SUPPORT AND MULTIFUNCTIONAL MATERIAL FOR THE CREATION OF PARTS AND FOR TISSUE ENGINEERING

(75) Inventors: Wei Sun, Cherry Hill, NJ (US); Jae Hyun Nam, Broomall, PA (US)

(73) Assignee: Drexel University, Philadelphia, PA (US)

( * ) Notice: Subject to any disclaimer, the term of this patent is extended or adjusted under 35 U.S.C. 154(b) by 2547 days.

(21) Appl. No.: 11/816,796

(22) PCT Filed: Feb. 24, 2006

(86) PCT No.: PCT/US2006/006404
§ 371 (c)(1),
(2), (4) Date: Sep. 26, 2007

(87) PCT Pub. No.: WO2006/093778
PCT Pub. Date: Sep. 8, 2006

(65) Prior Publication Data
US 2008/0145639 A1    Jun. 19, 2008

Related U.S. Application Data

(60) Provisional application No. 60/656,279, filed on Feb. 25, 2005.

(51) Int. Cl.
*B32B 3/26* (2006.01)
*B29C 65/00* (2006.01)
*A61L 31/14* (2006.01)
(Continued)

(52) U.S. Cl.
CPC ............... *A61L 31/146* (2013.01); *A61L 27/56* (2013.01); *B29C 67/0055* (2013.01); *B29C 67/0092* (2013.01); *B29L 2031/7532* (2013.01); *Y10T 156/10* (2015.01); *Y10T 428/249953* (2015.04)

(58) Field of Classification Search
CPC ........................ B29C 67/0055; B29C 67/0092
USPC ....................... 427/2.1, 2.24, 2.25; 428/304.4
See application file for complete search history.

(56) References Cited

U.S. PATENT DOCUMENTS 5,053,090 A    10/1991  Beaman et al.
5,260,009 A    11/1993  Penn
(Continued)

FOREIGN PATENT DOCUMENTS

WO   PCT/US2004/015316         5/2004

OTHER PUBLICATIONS

Reischmann M, Merz R, Schultz L, Weiss LE. Prototype implementation of an assembly system for tissue engineered constructs. Electrotechnik und Informationstechnik 2002; 7/8: 248-252.

(Continued)

*Primary Examiner* — Cachet Sellman
(74) *Attorney, Agent, or Firm* — Saul Ewing LLP; Kathryn Doyle; Brian R. Landry

(57) ABSTRACT

A solid freeform fabrication method of creating a three-dimensional article built at least in part from scaffolding layers, the method includes providing a scaffolding material, providing a supporting material in a shape of a foamy layer, and contacting the scaffolding material with the foamy layer to form at least one scaffolding layer and thereby creating the three dimensional article.

14 Claims, 4 Drawing Sheets

(51) Int. Cl.
  *A61L 27/56* (2006.01)
  *B29C 67/00* (2006.01)
  *B29L 31/00* (2006.01)

(56) References Cited

U.S. PATENT DOCUMENTS

| | | | |
|---|---|---|---|
| 5,503,785 A | 4/1996 | Crump et al. | |
| 5,514,232 A | 5/1996 | Burns et al. | |
| 5,663,883 A | 9/1997 | Thomas et al. | |
| 5,697,043 A | 12/1997 | Baskaran et al. | |
| 5,738,817 A | 4/1998 | Danforth et al. | |
| 5,807,437 A | 9/1998 | Sachs et al. | |
| 5,824,250 A | 10/1998 | Whalen et al. | |
| 5,876,550 A | 3/1999 | Feygin et al. | |
| 5,879,489 A | 3/1999 | Burns et al. | |
| 5,900,207 A | 5/1999 | Danforth et al. | |
| 5,916,585 A | 6/1999 | Cook et al. | |
| 5,997,681 A | 12/1999 | Kinzie | |
| 6,021,358 A | 2/2000 | Sachs | |
| 6,027,744 A | 2/2000 | Vacanti et al. | |
| 6,030,199 A | 2/2000 | Tseng et al. | |
| 6,066,285 A | 5/2000 | Kumar et al. | |
| 6,119,567 A | 9/2000 | Schindler et al. | |
| 6,139,574 A | 10/2000 | Vacanti et al. | |
| 6,143,293 A | 11/2000 | Weiss et al. | |
| 6,171,610 B1 | 1/2001 | Vacanti et al. | |
| 6,176,874 B1 * | 1/2001 | Vacanti et al. | 623/1.44 |
| 6,183,515 B1 | 2/2001 | Barlow et al. | |
| 6,231,879 B1 * | 5/2001 | Li et al. | 424/422 |
| 6,261,493 B1 * | 7/2001 | Gaylo et al. | 264/86 |
| 6,283,997 B1 | 9/2001 | Garg et al. | |
| 6,306,424 B1 | 10/2001 | Vyakarnam et al. | |
| 6,319,712 B1 | 11/2001 | Meenan et al. | |
| 6,333,029 B1 | 12/2001 | Vyakarnam et al. | |
| 6,337,198 B1 | 1/2002 | Levene et al. | |
| 6,365,149 B2 | 4/2002 | Vyakarnam et al. | |
| 6,375,880 B1 | 4/2002 | Cooper et al. | |
| 6,432,435 B1 | 8/2002 | Timmons et al. | |
| 6,454,811 B1 | 9/2002 | Sherwood et al. | |
| 6,534,084 B1 | 3/2003 | Vyakarnam et al. | |
| 6,547,994 B1 | 4/2003 | Monkhouse et al. | |
| 6,548,569 B1 | 4/2003 | Williams et al. | |
| 6,575,218 B1 | 6/2003 | Burns et al. | |
| 6,609,043 B1 | 8/2003 | Zoia et al. | |
| 6,623,687 B1 | 9/2003 | Gervasi et al. | |
| 6,730,252 B1 | 5/2004 | Teoh et al. | |
| 6,790,403 B1 | 9/2004 | Priedman, Jr. et al. | |
| 6,797,351 B2 | 9/2004 | Kulkarni et al. | |
| 2006/0105011 A1 | 5/2006 | Sun et al. | |

OTHER PUBLICATIONS

Weiss LE, Merz R, Prinz FB, Neplotnik G, Padmanabhan P, Shultz L, Ramaswami K. Shape deposition manufacturing of heterogeneous structures Journal of Manufacturing Systems 1997; 16(4): 239-248.

Xiong Z, Yan Y, Wang S, Zhang R, Zhang C. Fabrication of porous scaffolds for bone tissue engineering via low-temperature deposition. Scripta Materialia 2002; 46: 771-776.

Yan Y, Xiong Z, Hu Y, Wang S, Zhang R, Zhang C. Layer manufacturing of tissue engineering scaffolds via multi-nozzle deposition. Materials Letters 2003; 57: 2623-2628.

Landers R, Mülhaupt R. Desktop manufacturing of complex objects, prototypes and biomedical scaffolds by means of computer-assisted design combined with computer-guided 3D plotting of polymers and reactive oligomers. Macromol Mater Eng 2000; 282: 17-21.

Landers R, Mülhaupt R, John H. Desktop manufacturing and biofunctional processing. Kunststoffe/plast Europe 2001; 91 (12): 21-23.

Landers R, Hübner U, Schmelzeisen R, Mülhaupt R. Rapid prototyping of scaffolds derived from thermoreversible hydrogels and tailored for applications in tissue engineering. Biomaterials 2002; 23: 4437-4447.

Calvert P, O'Kelly J, Souvignier C. Solid freeform fabrication of organic-inorganic hybrid materials. Materials Science and Engineering 1998; C6: 167-174.

Vozzi G, Flaim CJ, Ahluwalia A, Bhatia S. Fabrication of PLGA scaffolds using soft lithography and microsyringe deposition. Biomaterials 2003; 24: 2533-2540.

Ang TH, Sultana FSA, Hutmacher DW, Wong YS, Fuh JYH, Mo XM, Loh HT, Burdet E, Teoh SH. Fabrication of 3D chitosan-hydroxyapatite scaffolds using a robotic dispensing system. Materials Science and Engineering 2002; C20: 35-42.

Vozzi G, Flaim CJ, Bianchi F, Ahluwalia A, Bhatia S. Microfabricated PLGA scaffolds: a comparative study for application to tissue engineering. Materials Science and Engineering 2002; C20: 43-47.

Mironov et al. Trends in Biotechnology 2003 21(4) :157-161.

* cited by examiner

LAYERED MANUFACTURING UTILIZING FOAM AS A SUPPORT AND MULTIFUNCTIONAL MATERIAL FOR THE CREATION OF PARTS AND FOR TISSUE ENGINEERING

BACKGROUND OF THE INVENTION

1. Field of the Invention

This invention relates to methods of creating scaffolds for artificial tissues and scaffolds and tissues made by these methods, specifically, the invention relates to methods utilizing depositing scaffolding material into a foamy substance to create soft tissues in a biologically friendly environment.

2. Description of Related Art

Tissue engineering is a rapidly developing field. The complexity of biological structures such as natural tissue have resulted in researchers exploring the techniques of rapid prototyping and other layered manufacturing techniques to create tissue constructs. Traditional methods of manufacturing are being adapted towards working within a biologically-friendly environment. This has led to the development of the new field of computer-aided tissue engineering (CATE). Solid freeform fabrication techniques (SFF) have been applied to create three dimensional shapes (3D shapes). SFF is a designation for a group of layered manufacturing techniques or processes that produce three dimensional shapes from additive formation steps. SFF, also known as Rapid Prototyping (RP), does not implement any part-specific tooling. A three dimensional part is produced from a 3D representation devised with the aid of a computer aided modeling program (CAD). This computer representation is a layer-by-layer slicing of a desired shape into consecutive two dimensional layers, which can then be fed to the control equipment to fabricate the desired part. SFF entails many different approaches to the method of fabrication. Stereolithography (SL), selective laser sintering (SLS), laminated object manufacturing (LOM), and fused deposition modelling (FDM) are examples of commercial processes applying SFF techniques.

Making scaffolds by layered manufacturing techniques requires the use of supporting structures such as, for example, sturdy surfaces or molds made of wax or polymeric foams. U.S. Pat. No. 5,503,785 to Crump, et al. details a method of creating breakaway supports for rapidly prototyped parts using a release coating. U.S. Pat. No. 6,797,351 to Kulkarni, et al. also describes methods for creating breakaway supports utilizing stereolithography. U.S. Pat. No. 5,053,090 to Beaman, et al. describes selective laser sintering where layers of powder are sintered with a laser. The unsintered powder acts as a support material and is later removed. U.S. Pat. No. 5,807,437 to Sachs, et al. uses a binder and powder system with the powder acting as a support material. U.S. Pat. No. 6,066,285 to Kumar, et al. describes using electrophotographic powder and a different support powder to build parts layer by layer. U.S. Pat. No. 6,030,199 to Tseng, et al. uses a method of depositing wax or other support materials during construction. After the part is completed, the support material is removed.

U.S. Pat. No. 6,790,403 to Priedeman, Jr., et al. describes an alkali-soluble support material that can be dissolved for a final product. U.S. Pat. No. 5,824,250 to Whalen et al. describes gel cast molding to create ceramic parts with dissolvable support materials. U.S. Pat. No. 6,375,880 to Cooper, et al. and U.S. Pat. No. 5,260,009 to Penn also describe the use of dissolvable support materials.

U.S. Pat. No. 5,697,043 to Baskaran, et al. describes a slurry made from a powder suspension in a gelling polysaccharide. A part layer is gelled and hardened, additional layers are added and hardened to eventually form the final part.

Many layered manufacturing techniques such as, for example, selective laser sintering, 3-D printing, fused deposition method, and stereolithography do not use foam as a support material. Much of the parts created using solid freeform fabrication and rapid prototyping techniques are too heavy to be supported by weak foams. Direct printing into a denser foam is difficult due to resistance and disturbs constructed layers. U.S. Pat. No. 6,021,358 to Sachs mentions the use of a foam, among other materials, as a removable filler material for rapid prototyping combined with subtractive processes.

Foams are used in a lost-foam technique for filling a mold. In the lost-foam technique, the foam is used as a temporary mold. Material is poured into the mold, destroying the foam and taking the shape of the mold. However, the method is just a variation of the lost-wax method of casting. U.S. Pat. No. 6,609,043 to Zoia, et al., describes using rapid prototyping methods to create molds filled by a foam.

U.S. Pat. Nos. 5,738,817 and 5,900,207 to Danforth, et al. utilize a dense foam base as a foundation substrate in a fused deposition method. However, the described foam material is inflexible and dense and has to be broken off or dissolved after the completion of the building process.

Other layered manufacturing methods also use sturdy foams as sheets or molds (see U.S. Pat. Nos. 5,514,232, 5,879,489, and 6,575,218 to Burns et al., U.S. Pat. No. 5,663,883 to Thomas et al., U.S. Pat. No. 5,997,681 to Kinzie, U.S. Pat. No. 6,119,567 to Schindler et al., and U.S. Pat. No. 5,876,550 to Feygin et al.).

Generally, the above techniques are not adapted for creating biologically active materials. These manufacturing techniques are geared up for creating "hard" parts found in inanimate objects, rather than "soft" or "wet" parts, that are found in biologically active systems. The use of light and pliable foams has not been explored by the current methods of rapid prototyping.

For biological scaffolds, the known applications of foams are limited to the creation of porous scaffold materials. U.S. Pat. No. 6,319,712 to Meenan et al. utilizes foams or other porous materials for artificial cartilage surfaces. U.S. Pat. No. 6,283,997 to Garg et al. describes using stereolithography to create porous ceramic structures for orthopedic implants. U.S. Pat. Nos. 6,306,424, 6,333,029, 6,365,149, and 6,534,084 to Vyakarnam et al. and U.S. Pat. No. 6,337,198 to Levene et al. disclose porous foam composites for tissue engineering. U.S. Pat. No. 6,548,569 to Williams, et al. describes using foams in medical devices. U.S. Pat. No. 6,432,435 to Timmons, et al. discloses creating keratin-based films, foam scaffolds, and sheets. Thus, in these patents, foams are used as a structural component such as, for example, a sheet of metal or an aluminum rod or a ceramic plate.

Layered manufacturing techniques have gained increased interest in the field of tissue engineering due to their ability to create complex parts and various geometries. Some of these industrial methods have been modified to be performed in a liquid and sterile environment to accommodate working with biological factors and cells.

Reischmann and Weiss et al. described a method for building bone tissue scaffolds using laminated sheets of material and stacking them together [1, 2]. Yan and Xiong et al. disclosed the concept of using layered manufacturing methods and multi-nozzle deposition extrusion and jetting processes [3, 4]. R. Landers, et al. devised a SFF method using a syringe-based system to dispense liquids, which is suitable for working with biological materials such as cells and hydrogels [5, 6, 7]. Calvert et al. devised a syringe-based system for the extrusion of hybrid polymer materials embedded with glass using layered SFF manufacturing [8]. Vozzi et al. devised a microsyringe deposition system [9, 10]. Ang et al. created a single-nozzle automated extrusion system that can utilize basic STL files [11]. U.S. Pat. Nos. 6,139,574 and 6,176,874 to Vacanti et al. disclose vascularized tissue regeneration matrices formed by solid free form fabrication techniques. U.S. Pat. No. 6,143,293 to Weiss, et al. discloses assembled scaffolds for three dimensional cell culturing and tissue generation. U.S. Pat. Nos. 6,027,744 and 6,171,610 to Vacanti et al. describe guided development and support of hydrogel-cell compositions. U.S. Pat. No. 6,454,811 to Sherwood et al. discloses composites for tissue regeneration and methods of manufacture thereof. U.S. Pat. No. 6,547,994 to Monkhouse et al. describes a process for rapid prototyping and manufacturing of primarily drug delivery systems with multiple gradients, mostly involving the three dimensional printing (3DP) technique. U.S. Pat. No. 6,623,687 to Gervasi et al. describes a process for making three-dimensional objects by constructing an interlaced lattice construct using SFF to create a functional gradient material. U.S. Pat. No. 6,183,515 to Barlow et al. utilizes selective laser sintering to create calcium phosphate bone implants.

The adaptation of these techniques for biological purposes has many obstacles. Many of the methods, such as laser sintering, stereolithography, fused deposition, and 3-D printing, create parts under operating conditions that are environmentally hostile to cell viability. These methods use high temperatures, powders, chemicals, and so forth, that does not allow cells to be introduced into the part during manufacture. These methods are only suitable for creating "hard" scaffolds that can be cleaned and processed with cells being introduced at a later time.

However, there is also a need for creating "soft" scaffolds, such as hydrogel-based scaffolds, that can sustain viable cells during manufacture. The creation of a syringe based system within a liquid environment was the next step to try to solve this problem. This technique allows printing into liquids or use low temperature to freeze the liquid to act as a support material during construction of a scaffold [12]. The liquid acts as a crosslinker to polymerize the deposited solution.

The disadvantage of the method of printing into a liquid solution is that the density of the deposited solution is very similar to the density of the liquid it is being deposited into, so that the deposited solution can be easily disturbed and can float or drift. This problem can be alleviated to some extent if the liquid level is increased in a layer-by-layer fashion and is properly regulated. However, the height of the liquid level will vary depending upon the height of the layer being constructed. Thus, slight inaccuracies in calculations multiply by each additional layer. Also, if there is a trapped air, or if the scaffold is less dense than the liquid, the buoyancy can be disruptive, and results in the part having a tendency to float.

Filaments and struts may also tend to float during the manufacturing process so that the resulting part would have features that are not as sharp or well-defined as desired. Many of the known techniques print into a crosslinking solution to create the final scaffold. Differences in density between the scaffold and the liquid solution can create problems as described above. The liquid itself does not provide much stability to the structure. In addition, the liquid may transmit forces and vibrations from the mechanical apparatus that may reduce the precision of the device. Further, there may also be diffusion of biological and chemical factors or components during the manufacturing process, especially for the construction of large tissue engineered constructs.

"Soft" parts need to have supporting structures in order to ensure stability during their manufacture. Arches and bridge-like features need support against gravity, even in a liquid environment of a similar density. To address these needs, the liquid solution could be made denser, but this would cause problems with buoyancy and viscosity. In addition, the moving parts such as a print head or a nozzle will impart forces to the previously deposited layer while traveling above it through the viscous fluid.

In current rapid prototyping and solid freeform fabrication techniques, foam is not generally used as a supporting material but as a building material and is generally dense or solidified to create "hard" parts. The known techniques are not as well developed for creating "soft" parts that are common in biological components such as soft tissue.

For biologically active scaffolds, foam is also used as a structural component due to its porous architecture. Current manufacturing techniques are a modification of industrial techniques developed for manufacturing of "hard" parts, and are not well-adapted for biological conditions due to harsh manufacturing conditions such as high temperatures, harmful chemicals, and other environmental conditions.

Newer techniques are designed to create "soft" tissue components within a liquid environment that is much more conducive to cell growth and survival. However, these methods have limitations in the manufacturing process and do not result in creating well-defined reproducible parts. Despite the foregoing developments, there is a need in the art for improved methods of making scaffolds or parts suitable for accommodation and sustaining of biologically active substances, wherein these scaffolds or parts are made to be more reproducible and more precise in their dimensions.

All references cited herein are incorporated herein by reference in their entireties.

BRIEF SUMMARY OF THE INVENTION

The invention is a method for utilizing a foam for fabrication of tissue scaffolds using layered manufacturing techniques. The advantage of using a foam is that it has properties that are well suited for creation of "soft" components such as those used in tissue engineering and for biological constructs. In the invention, the foam is used as a support to help stabilizing soft, gel-like structures, and can also be mixed with a crosslinker to polymerize deposited scaffolding materials. The foam thus serves multiple purposes with significant advantages over the prior art. The present invention includes a solid freeform fabrication method of creating a three-dimensional article built at least in part from scaffolding layers, the method comprising providing a scaffolding material, providing a supporting material in a shape of a foamy layer, and contacting the scaffolding material with the foamy layer to form at least one scaffolding layer and thereby creating the three dimensional article.

In certain embodiments, the scaffolding material is deposited on a top outer surface of the foamy layer and/or inside the foamy layer.

In certain embodiments, the supporting material comprises a foaming agent and optionally a crosslinking agent.

In certain embodiments, the foaming agent is a member selected from the group consisting of anionic surfactants, cationic surfactants, amphoteric surfactants, non-ionic surfactants, hydrolized protein and fluorocarbon surfactants. In certain embodiments, the crosslinking agent is calcium chloride.

In certain embodiments, the scaffolding material is a member selected from the group consisting of alginate, chitosan, collagen, fibrin, salts and derivatives thereof.

In certain embodiments, the supporting material further comprises a biologically active agent. In certain embodiments, the biologically active agent is a member selected from the group consisting of cells, nucleic acids, proteins, and pharmacologically active agents.

In certain embodiments, the supporting material further comprises at least one of a surface modifier and a sterilizing agent.

In certain embodiments, the method further comprises depositing the supporting material simultaneously with the scaffolding material such that the supporting material is retained within the three dimensional article. In some variants of this embodiment, the supporting material comprises the foaming agent, the crosslinking agent and optionally the biologically active agent. In some variants of this embodiment, the supporting material further comprises a surface modifier and/or a sterilizing agent.

Also provided is a three-dimensional article manufactured by the method of the invention. In certain embodiments, the three dimensional article is an artificial tissue. In certain embodiments, artificial tissue is made from the scaffolding material which comprises at least one of alginate, chitosan, collagen, fibrin, salts and derivatives thereof.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The invention was driven by a desire to develop a method for fabricating a three dimensional article using solid freeform fabrication techniques, wherein the three dimensional article is built on a foamy, spongy or frothy supporting material rather than on a liquid support and therefore avoid problems created by difference in density between scaffolding materials and supporting materials. Accordingly, the invention includes a solid freeform fabrication method of creating a three-dimensional article built at least in part from scaffolding layers, the method comprising providing a scaffolding material, providing a supporting material in a shape of a foamy layer, and contacting the scaffolding material with the foamy layer to form at least one scaffolding layer and thereby creating the three dimensional article.

The inventors have discovered that the above described shortcomings of utilizing liquids as a printing medium can be overcome by printing into a foam instead of a liquid solution. The foam is less dense than the part or a scaffold being built so there are no problems with buoyancy and less drift of parts during the manufacturing process. The foam helps in supporting the scaffolding structure against gravity. Recognizing these principles, inventors utilize the foam in the present invention as a scaffolding environment to help keep the part in place during the manufacturing process, creating sharply defined edges and features and making reproducible parts.

Figure 2A:
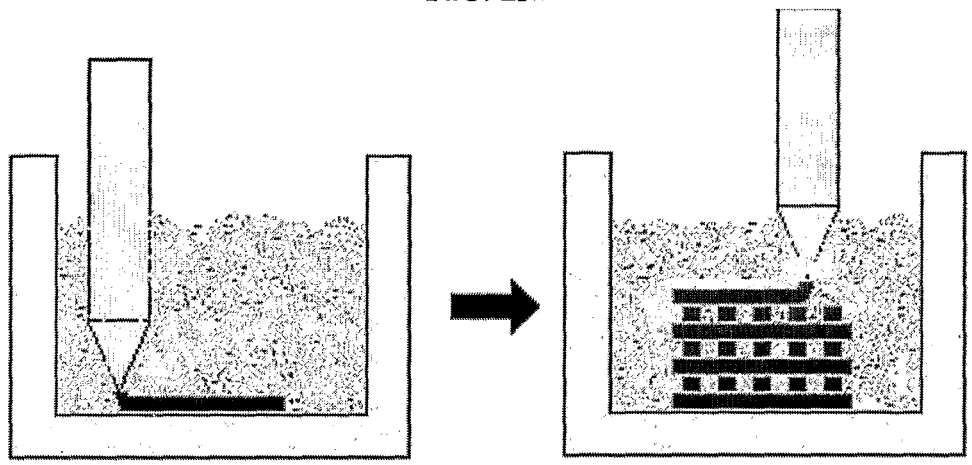
FIGS. 2A-2C are schemes that illustrate methods of constructing a three-dimensional article by submerging the nozzle into a foam (FIG. 2A), by adding foam in a layer-by-layer fashion (FIG. 2B), and/or by dropping material on top of a foam (FIG. 2C).
Figure 2B:
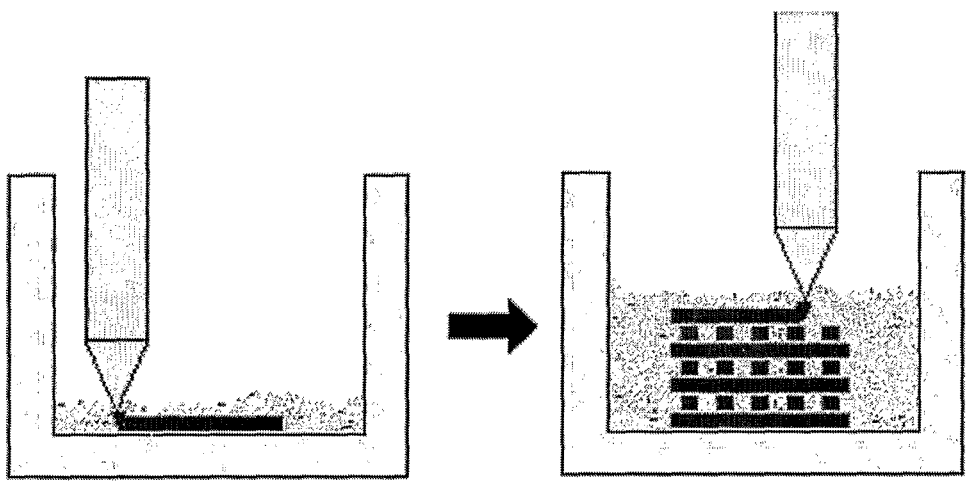
Figure 2C:
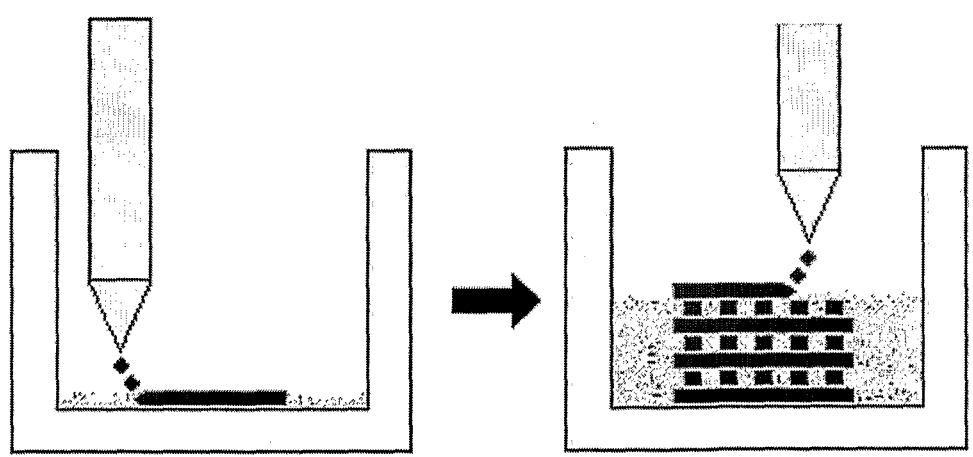

Non-limiting ways to deposit scaffolding material into the foam in the method of the invention are illustrated in FIGS. 2A-2C. The foam can be added in a layer-by-layer fashion (FIGS. 2B-2C) or the printing nozzle can be submerged into the foam with printing done directly within the foam (FIG. 2A). Advantageously, since the invention uses a light foam as distinguished from solid and dense foams (e.g., styrofoams), printing nozzles can freely move around within the foam without disrupting the part being formed as it would in a liquid. Thus, the foam has the advantages associated with printing into a liquid medium, without the disadvantages described above. Ability to print within the foam environment will prevent deforming (e.g., curling) or disturbing outer surfaces of scaffolds during construction, as it happens, for example in a 3D printing method utilizing a powder and a binder; printing within the foam provides a protective shield (i.e., a homogeneous environment) that isolates the deposited layer from the outer environment and protects from changes in physical parameters.

Advantageously, due to the structural support provided by the foam, larger hydrogel structures can be created in this fashion than that if printing into a liquid solution. Further, the structural support provided by foam is three-dimensional while the support materials in the existing art generally just hold the part up against gravity. Another advantage of the present invention is in that initial diffusion of the chemicals and biological factors will be limited within a foam material.

The foam that is useful in this invention is defined as (1) a light frothy mass of porous bubbles or membranes formed in or on the surface of a liquid or (2) a stabilized froth produced chemically or mechanically. The foam of the present invention is a soft pliable substance and is distinguished from a solid substance. The foam of the present invention is made from a foaming agent by methods known in the art, such as, for example, vigorous mixing, gas sparging, etc. The term "foamy layer" as used herein includes a layer comprising the foam, wherein the term "layer" is not limited to a contiguous surface, shape or to any height, length or width.

The foaming agent is a substance that is used to create the foam which would have the characteristics described above. Non-limiting examples of foaming agents are surfactants such as anionic surfactants, cationic surfactants, amphoteric surfactants, non-ionic surfactants, hydrolized protein and fluorocarbon surfactants. Other examples of foaming agents include chemicals capable of forming a soft foam or a froth in which nozzles or print heads for depositing the scaffolding material can freely move.

Non-limiting examples of anionic surfactants are alkyl phosphate, ammonium dodecyl benzene sulfonate, ammonium lauryl sulfate, ammonium polyoxyethylene aryl ether sulfate, ammonium polyoxyethylene nonylphenyl ether sulfate, calcium dodecylbenzene sulfanate, cetyl phosphate, disodium cocamido MIPA sulfosuccinate, disodium laureth-3 sulfosuccinate, disodium ricinoleamido MEA-sulfocuccinate, dodecylbenzene sulfonic acid, laureth-3-phosphate, lauryl phosphate, linear alkylbenzene sulfonic acid, mono alkyl ether phosphate, mono alkyl phosphate, mono lauryl phosphate, mono oleyl ether hosphate, nonyl phenol 10 EO phosphate, oleth-3-phosphate, pleyl phosphate, phosphate ester, sodium alkyl diphenyl ether disulfonate, sodium alkyl disufate, sodium alkyl benzene sulfonate linear, sodium cetyl glutamate, sodium cocoyl isethionate, sodium cocoyl methyltaurate, sodium cocoyl sarcosinate, sodium dioctyl sulfosuccinate, sodium dodecyl benzene sulfonate, sodium laureth-3-sulfate, sodium lauroyl glutamate, sodium lauroyl sarcosinate, sodium lauryl ether sulfate, sodium lauryl glutamate, sodium lauryl sulfate, sodium linear alkylbenzene sulfonate, sodium octyl sulfate, sodium olyoxyethylene aryl ether sulfate, sodium polyoxyethylene nonylphenyl ether sulfate, sodium undecenyl glutamate, sodium xylene sulfonate, triethanolamine cocoyl glutamate, triethanolamine lauryl sarcosinate, triethanolamine lauryl sulfate, triethanolamine lauroyl sarcosinate, triethanolamine lauryl sulfate.

Non-limiting examples of cationic surfactants are behenyl trimethyl ammonium chloride, bis(acyloxyethyl) hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowdimonium chloride, guar hydroxypropyltrimonium chloride, lauralkonium chloride, lauryl dimethylamine oxide, lauryl dimethylbenzyl ammorium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, stearyl dimethylbenzyl ammonium chloride, stearyl trimethyl ammonium chloride, trimethylglycine.

Non-limiting examples of amphoteric surfactants are alkyl betaine, cocamidopropyl betaine, cocamidopropyl betaine, monoglyceride, cocamidopropyl hydroxysultaine, cocamidopropylamine oxide, cocoamidopropyl betaine, cocoampho carboxyglycinate, cocoampho carboxyglycinate, sodium lauryl sulfate, cocoampho dipropionate, cocoampho glycinate, cocoamphodipropionate, lauramidopropyl beatine, lauramine oxide, lauryl betaine, lauryl hydroxysultaine, myristamine oxide, sodium cocamphoacetate, and sodium lauroamphoacetate.

Non-limiting examples of non-ionic surfactants are cetyl octanoate, cocoamide DEA, cocoamide MEA, cocoamido propyl dimethyl amine oxide, coconut fatty acid diethanol amide, coconut fatty acid monoethanol amide, diglyceryl di isostearate, diglyceryl mono isostearate, diglyceryl mono laurate, diglyceryl mono oleate, ethylene glycol di stearate, ethylene glycol mono stearate, ethyoxylated castor il, glyceryl mono isostearate, glyceryl mono laurate, glyceryl mono myristate, glyceryl mono oleate, glyceryl mono stearate, glyceryl tri caprylate/caprate, glyceryl tri isostearate, glyceryl tri oleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene fatty ester, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethylene oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol mono stearate, sorbitan mono laurate, sorbitan mono oleate, sorbitan mono palmitate, sorbitan mono stearate, sorbitan sesqui oleate, sorbitan tri oleate, stearamide DEA, stearic acid diethanol amide, and stearic acid monoethanol amide.

In certain embodiments, the foaming agent is an alkyl glyceryl sulfonate (AGS), preferably AGS-1214.

In certain embodiments, the supporting material comprises the foaming agent mixed with a cross-linking agent to facilitate curing of scaffolding materials being deposited. Non-limiting examples of cross-linking agents are calcium chloride or barium chloride for alginates, thrombin for fibrinogen, and sodium hydroxide or glutaraldehyde for chitosan.

In certain embodiments, the supporting material further comprises a biologically active agent. In certain embodiments, the biologically active agent is a member selected from the group consisting of cells, nucleic acids, proteins, and pharmacologically active agents. In certain embodiments, the supporting material further comprises a surface modifier and/or a sterilizing agent.

A scaffolding agent is a homogeneous substance or a heterogeneous mixture of multiple substances which form a scaffold of the three-dimensional article of the invention. Non-limiting examples of scaffolding agents useful in this invention are polysaccharides such as, for example, alginate, chitosan, collagen, fibrin or salts and derivatives thereof, hyaluronic acid, agar, polyethylene glycol and its copolymers, acrylamide-based and acrylic acid-based polymers, polycaproactone, tricalcium phosphate, hydroxyapatite, polyglycolic acid, polylactic acid, and co-polymers thereof, polyhydroxybutyrate, polypropylene fumarate, and bioactive glasses.

In certain embodiments, the scaffolding material is deposited on a top outer surface of the foamy layer and/or inside the foamy layer.

In certain embodiments, the method further comprises depositing the supporting material simultaneously with the scaffolding material such that the supporting material is retained within the three dimensional article. In some variants of this embodiment, the supporting material comprises the foaming agent, the crosslinking agent and optionally the biologically active agent. In some variants of this embodiment, the supporting material further comprises a surface modifier and/or a sterilizing agent.

The foam can also be removed or retained or further modified as part of the scaffold structure. The foam could be solidified after the article is built. Moreover, using the existing techniques, such as, for example, particulate leaching, the foam could be modified into an open porous structure.

In the method of the invention, the scaffolding material is deposited onto the foam from a nozzle or another dispenser. The term "deposited" includes being extruded deposited as microdroplets or any other form of transferring onto the supporting surface.

The density of the foams could be increased such that it can support microdroplets of material dropped on top of it. Creating overarching structures using hydrogels by using a microdroplet deposition method into a liquid is difficult. The use of foams makes this possible.

Figure 1:
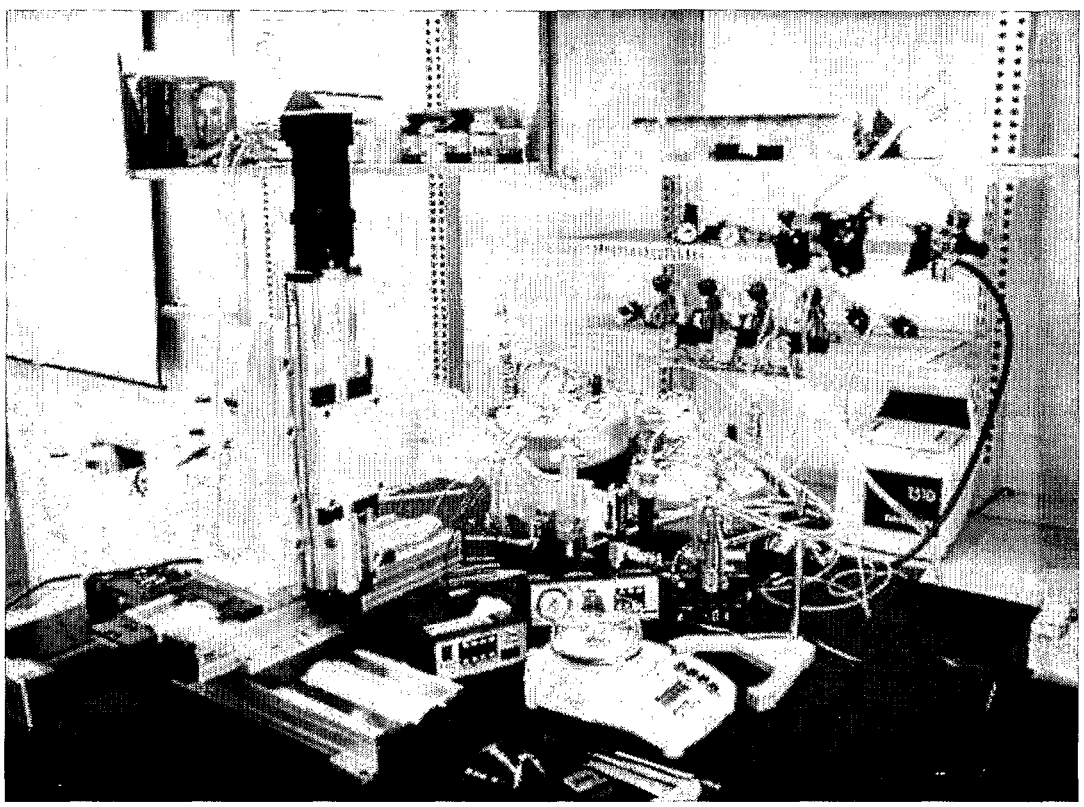
FIG. 1 is a photograph illustrating a computer-aided tissue engineering system.

The method of the invention can be demonstrated utilizing an exemplary automated, computer-aided tissue engineering (CATE) system (see FIG. 1) or a system described in a PCT application Serial No. PCT/US2004/015316 filed on May 14, 2004 by inventors incorporated herein in its entirety. The CATE system consists of a user interface that can import a design built within a CAD environment or data taken from biomedical instruments such MRI or CT. The system can also use simple, automated programs directly written by the user as well.

The automated system takes the data and translates it into instructions for the path of the printhead in the x, y, and z-axis to build the part in a layer-by-layer fashion. The multi-nozzle head can print heterogeneous materials simultaneously within each layer. The nozzles can use a variety of different methods of material delivery such as extrusion, droplet deposition, fused deposition, and spraying among many other methods. In the preferred embodiment, the scaffolding material is sodium alginate, which is deposited by a pneumatically actuated valve into a foam made from a foaming agent alkyl glyceryl sulfonate containing a crosslinking salt solution, such as calcium chloride. For experimental purposes, 3% w/v solutions of sodium alginate, and 1% and 5% w/v solutions of calcium chloride were used; however, a wide range of compositions can be used depending upon the desired properties of the material.

The scaffolding material can also contain additional materials such as, for example, hydroxyapatite or polypeptide moieties such as RGD peptides to improve cell adhesion.

Pressures can be varied from almost zero psi to over 14 psi, depending upon the flow rate desired and the travel speed of the printhead. For the 1% w/v solution, 2.52 psi was used. For the 5% w/v solution, 0.62 psi was used. The speed of the printhead was 2 mm/s, but can also be varied depending upon the desired precision and time required for part construction. The inner diameter of the nozzle was 0.41 mm. This can also be modified to adjust the flow rate and the thickness of the filaments deposited. The height increment was 0.600 mm per layer.

To create the foam, the foaming agent such as, for example, polyethylene glycol (PEG) and/or other stabilizers or surfactants such as alkyl glyceryl sulfonate and other commercially available products for generating and stabilizing foams is treated as described be methods known in the art, such as, for example, vigorous mixing and gas blowing. In certain embodiments, the foaming agent or a foam are mixed with the crosslinking solution to create a multifunctional foam that simultaneously supports the parts being created and also cures or crosslinks the scaffolding material being deposited by the nozzle.

The foam can be added in a very thick layer with the printhead and nozzles being submerged within the foam during the printing process (see FIG. 2A). This method has the advantage of being very simple without a need to calculate the amount of foam that has to be added per layer. The foam can also be added in a very thin layer-by-layer fashion as the part is being built up (see FIG. 2B). Denser foam can be added in a layer-by-layer fashion with the scaffolding material being deposited on top of the foam (see FIG. 2C).

Figure 3A:
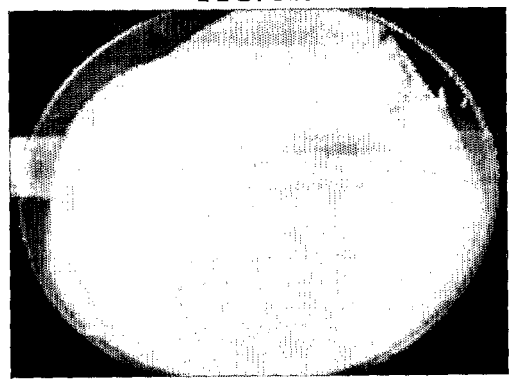
FIGS. 3A and 3B are photographs of tissue scaffold constructs created within foam using layered manufacturing techniques. The scaffolds illustrated are approximately 20 mm×20 mm×12 mm in size having about 20 scaffolding layers.
Figure 3B:
Figure 5:
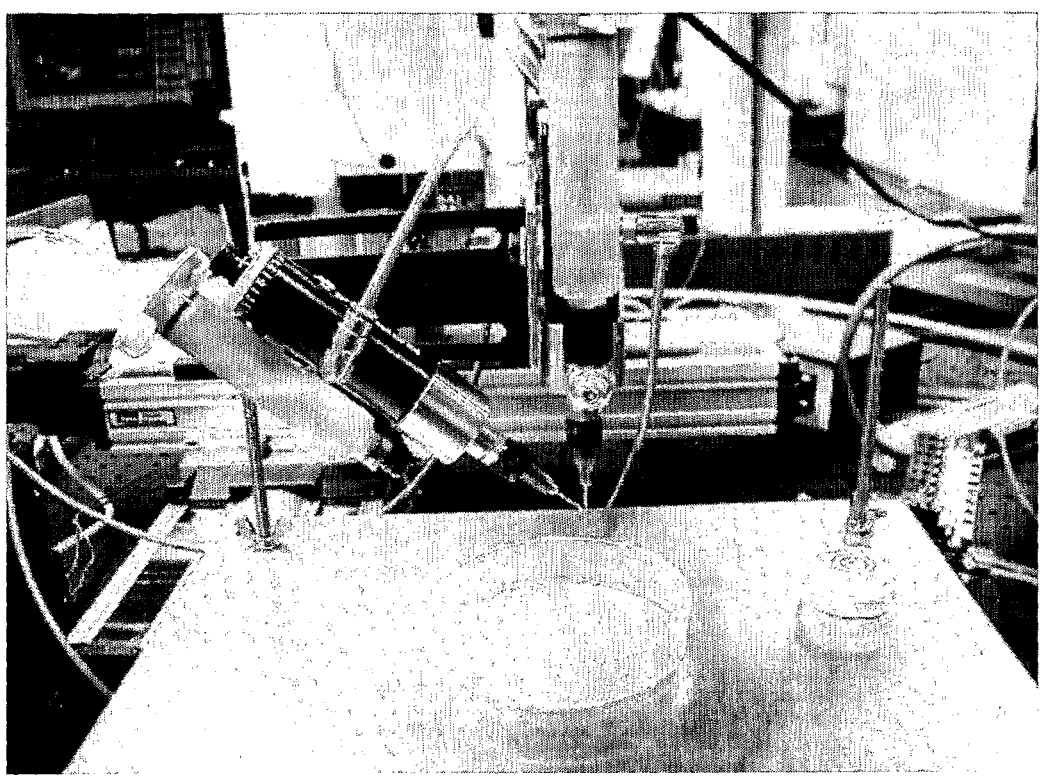
FIG. 5 is a photograph of a two syringe based system which demonstrates a concept of the method of the invention allowing a multi staged or simultaneous depositing of a scaffolding material and a foam.

Multiple methods were used to construct the tissue scaffold illustrated (see FIGS. 3A, 3B, and 5). The sizes of the constructs were 20 mm×20 mm×12 mm. They consisted of 20 scaffolding layers with a height of 0.600 mm per layer.

Figure 4:
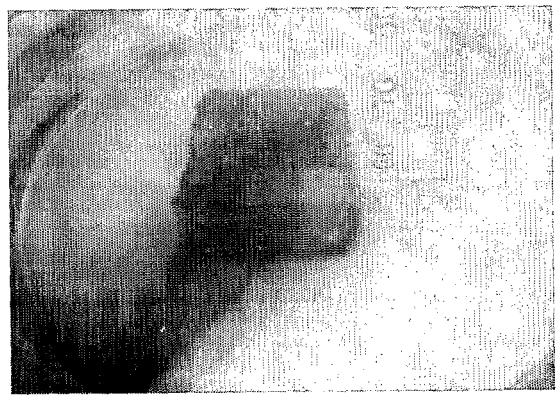
FIG. 4 is a photograph of a resulting scaffold wherein the foam is removed by rinsing.

Upon completion of the construction process, post-processing of the part is done by rinsing the part with a calcium chloride or other solution to remove the foam and to also increase the crosslinks and bonding between layers to reduce delamination from shear and other stresses (see FIG. 4). The duration of the time immersed in the crosslinking solution can be increased to improve structural strength.

Removal of the foam can be improved by rinsing the part with a solution that reduces the surface tension of the foam, thereby breaking apart the foam. Various defoaming agents that are commercially available can be used to remove the foam such as polydimethylsiloxane based compounds; non-silicone, water-based products; polypropylene glycol based compounds; and petroleum derivatives. Some of these defoaming agents have low biotoxicity and are often used in food products.

Additional post-processing techniques can be used to improve the bioactive behavior of the scaffold. Coatings can be added to enhance cell adhesion, filler materials such as fibrin, chitosan, or collagen could be added as well for the desired biological properties.

In certain embodiments of the method, the foam is not removed, but is retained within the structure. The problem with foam is that it traps air and may be restrictive to cell migration and travel. It is not an open porous structure with good connectivity, thus the foam should be combined with materials that can be leached out to create an open porous structure.

In certain embodiments of the method, a foam contains additional materials designed to strengthen it, e.g., crosslinking agents, or to provide biological functionality, e.g., cells, proteins, antibiotics and the like.

Natural surfactants using biological proteins can also be mixed with the crosslinking solution to create the foam.

In certain embodiments, the method does not require CAD systems and can rely upon simplified computer programs or commands directing the shape of the part being built.

In certain embodiments of the method, the scaffolding material includes other gel-like materials such as, for example, chitosan, fibrin, modified alginates, as well as sturdier materials such as polycaprolactone and other plastics, and slurries containing ceramic and other powders, hydroxyapatite, or tricalcium phosphate.

In certain embodiments of the method, the foam can act as a cooling media for the scaffolding material if there is a chemical reaction, or if the article that is being created has to be heated. In that, the scaffolding material and the foam would have different temperatures.

Tissue constructs can be created under biologically suitable conditions by printing into liquid solutions. Printing into liquid solutions, however, has disadvantages. The primary problem is the density issue resulting in parts that can be disturbed or can float and drift. "Soft" biologically-designed parts will need to have supporting structures in order to ensure stability against gravity.

Printing into a foam solution has many of the advantages of printing into a liquid solution, but without the disadvantages. In the preferred embodiment, the foam is combined with a crosslinking solution that polymerizes the extruded material being deposited from the nozzle. In alternative embodiments, the foam does not need to be mixed with a polymerizing agent. The foam is less dense so there are no problems with buoyancy. The foam acts as a scaffold that supports the parts being constructed and helps in supporting the hydrogel or "soft" structure against gravity. Because of the structural support provided by the foam, large hydrogel structures can be created. As shown in FIG. 5, a two syringe based system demonstrates a concept of the method of the invention allowing a multi staged or simultaneous depositing of a scaffolding material and a foam. An additional syringe (not shown) can also be provided to deliver other components such as for example, a crosslinking agent allowing the foam to have not only a supporting function, but also to polymerize the scaffolding material. Examples of other components are a surface modifier, a sterilizing agent, and a biologically active agent which could be delivered from separate nozzles or mixed to be delivered as a mixture from one ore more nozzles.

The foam can be added in a layer-by-layer fashion or a printhead mechanism can be submerged directly into the foam. In additional embodiments, the foam can be retained or further modified as part of the finished product.

Examining the current rapid prototyping and solid freeform fabrication techniques, foams are not used extensively or to full advantage. When they are used, it is simply as a building material and is generally dense or solidified to create "hard" parts. Manufacturing techniques are not as well developed for creating "soft" and "wet" parts that are common in biological components such as soft tissue.

This same mentality is carried into the biological field where foams are also used as a structural material, often solely for its porous architecture. Current biological manufacturing techniques are often just modification of industrial techniques, and are not well-adapted for biological conditions.

The use of foams as a printing medium is a novel method for creating biologically-oriented parts such as tissue scaffolds and constructs. However, the use of foam in this manner isn't just restricted to the field of tissue engineering, but can be applied towards the creation of "soft" components in other manufacturing industries. The merging of biology with other areas, such as computing, has resulted in the development of biochips and biosensors. A further continuation of the trend may result in the development of manufacturing techniques that create products that are more organic and life-like, "wet" and "squishy". Manufactured products of the future may have a distinct biological quality to them that is radically different from the metal and plastic parts that we are so familiar with.

Also provided is a three-dimensional article manufactured by the method of the invention. In certain embodiments, the three dimensional article is an artificial tissue.

While the invention has been described in detail and with reference to specific examples thereof, it will be apparent to one skilled in the art that various changes and modifications can be made therein without departing from the spirit and scope thereof.

REFERENCES

[1] Reischmann M, Merz R, Schultz L, Weiss L E. Prototype implementation of an assembly system for tissue engineered constructs. *Electrotechnik und Informationstechnik* 2002; 7/8:248-252.
[2] Weiss L E, Merz R, Prinz F B, Neplotnik G, Padmanabhan P, Shultz L, Ramaswami K. Shape deposition manufacturing of heterogeneous structures *Journal of Manufacturing Systems* 1997; 16(4): 239-248.
[3] Xiong Z, Yan Y, Wang S, Zhang R, Zhang C. Fabrication of porous scaffolds for bone tissue engineering via low-temperature deposition. *Scripta Materialia* 2002; 46: 771-776.
[4] Yan Y, Xiong Z, Hu Y, Wang S, Zhang R, Zhang C. Layer manufacturing of tissue engineering scaffolds via multi-nozzle deposition. *Materials Letters* 2003; 57: 2623-2628.
[5] Landers R, Mülhaupt R. Desktop manufacturing of complex objects, prototypes and biomedical scaffolds by means of computer-assisted design combined with computer-guided 3D plotting of polymers and reactive oligomers. *Macromol Mater Eng* 2000; 282: 17-21.
[6] Landers R, Mülhaupt R, John H. Desktop manufacturing and biofunctional processing. *Kunststoffe/plast Europe* 2001; 91 (12): 21-23.
[7] Landers R, Hübner U, Schmelzeisen R, Mülhaupt R. Rapid prototyping of scaffolds derived from thermoreversible hydrogels and tailored for applications in tissue engineering. *Biomaterials* 2002; 23: 4437-4447.
[8] Calvert P, O'Kelly J, Souvignier C. Solid freeform fabrication of organic-inorganic hybrid materials. *Materials Science and Engineering* 1998; C6: 167-174.
[9] Vozzi G, Flaim C J, Bianchi F, Ahluwalia A, Bhatia S. Microfabricated PLGA scaffolds: a comparative study for application to tissue engineering. *Materials Science and Engineering* 2002; C20: 43-47.
[10] Vozzi G, Flaim C J, Ahluwalia A, Bhatia S. Fabrication of PLGA scaffolds using soft lithography and microsyringe deposition. *Biomaterials* 2003; 24: 2533-2540.
[11] Ang T H, Sultana F S A, Hutmacher D W, Wong Y S, Fuh J Y H, Mo X M, Loh H T, Burdet E, Teoh S H. Fabrication of 3D chitosan-hydroxyapatite scaffolds using a robotic dispensing system. *Materials Science and Engineering* 2002; C20: 35-42.
[12] Xiong Z, Yan Y, Wang S, Zhang R, Zhang C. Fabrication of porous scaffolds for bone tissue engineering via low-temperature deposition. *Scripta Materialia* 2002; 46: 771-776

What is claimed is:

1. A solid freeform fabrication method of creating a three-dimensional article built at least in part from scaffolding layers, the method comprising:
   providing a scaffolding material;
   providing a supporting material in a shape of a foamy layer; and
   contacting the scaffolding material with the foamy layer to form at least one scaffolding layer and thereby creating the three dimensional article.

2. The method of claim 1, wherein the scaffolding material is deposited on a top outer surface of the foamy layer, inside the foamy layer or both.

3. The method of claim 1, wherein the supporting material comprises a foaming agent.

4. The method of claim 1, wherein the supporting material comprises a foaming agent and a crosslinking agent.

5. The method of claim 4, wherein the foaming agent is a member selected from the group consisting of anionic surfactants, cationic surfactants, amphoteric surfactants, non-ionic surfactants, hydrolyzed protein and fluorocarbon surfactants.

6. The method of claim 4, wherein the crosslinking agent is a member selected from the group consisting of calcium chloride, barium chloride, thrombin, sodium hydroxide and glutaraldehyde.

7. The method of claim 1, wherein the scaffolding material is a member selected from the group consisting of alginate, chitosan, collagen, fibrin, salts and derivatives thereof.

8. The method of claim 1, wherein the supporting material further comprises a biologically active agent.

9. The method of claim 8, wherein the biologically active agent is a member selected from the group consisting of cells, nucleic acids, proteins, and pharmacologically active agents.

10. The method of claim 1, wherein the supporting material further comprises at least one of a surface modifier or a sterilizing agent.

11. The method of claim 1, further comprising depositing the supporting material simultaneously with the scaffolding material such that the supporting material is retained within the three dimensional article.

12. The method of claim 11, wherein the supporting material comprises a foaming agent, a crosslinking agent and optionally a biologically active agent.

13. The method of claim 12, wherein the supporting material further comprises at least one of a surface modifier or a sterilizing agent.

14. The method of claim 1, wherein the foamy layer acts as a cooling media for the scaffolding material.

* * * * *